(12) United States Patent
Baynham

(10) Patent No.: US 8,500,783 B2
(45) Date of Patent: Aug. 6, 2013

(54) DYNAMIC CERVICAL PLATE WITH SPACER

(75) Inventor: Matthew G. Baynham, Jupiter, FL (US)

(73) Assignee: Atlas Spine, Inc., Jupiter, FL (US)

( * ) Notice: Subject to any disclaimer, the term of this patent is extended or adjusted under 35 U.S.C. 154(b) by 367 days.

(21) Appl. No.: 12/433,399

(22) Filed: Apr. 30, 2009

(65) Prior Publication Data

US 2009/0275988 A1    Nov. 5, 2009

Related U.S. Application Data

(60) Provisional application No. 61/049,209, filed on Apr. 30, 2008.

(51) Int. Cl.
*A61B 17/66* (2006.01)

(52) U.S. Cl.
USPC .......................................................... 606/282

(58) Field of Classification Search
USPC ......... 606/248, 249, 96, 104, 86 A, 280–299, 606/105, 246, 251–261; 623/17.16, 17.11
See application file for complete search history.

(56) References Cited

U.S. PATENT DOCUMENTS

| | | | |
|---|---|---|---|
| 5,620,443 A | 4/1997 | Gertzbein et al. | |
| 6,017,345 A | 1/2000 | Richelsoph | |
| 6,106,557 A * | 8/2000 | Robioneck et al. | 623/17.15 |
| 6,136,002 A | 10/2000 | Shih et al. | |
| 7,435,261 B1 * | 10/2008 | Castro | 623/17.11 |
| 2003/0060828 A1 | 3/2003 | Michelson | |
| 2005/0177160 A1 * | 8/2005 | Baynham et al. | 606/69 |
| 2007/0270965 A1 * | 11/2007 | Ferguson | 623/17.11 |
| 2007/0276371 A1 * | 11/2007 | Baynham et al. | 606/61 |

* cited by examiner

*Primary Examiner* — Andrew Yang
*Assistant Examiner* — Diana S Jones
(74) *Attorney, Agent, or Firm* — McHale & Slavin, P.A.

(57) ABSTRACT

Disclosed is a dynamic cervical plate system that may be adjusted to length, locked in place to provide compression, and will automatically shorten its length to maintain compression. The system includes spinal cages coupled to the plate which provide intervertebral spacers for excised discs. The cervical plate system has a flat elongated shaft adapted to span the intervertebral space and has at least two screw receivers spaced along the length of the plate. The screw receivers each have screw holes for accepting the heads of bone screws. The spinal cage is coupled to the plate and interposed between the screw receivers.

10 Claims, 10 Drawing Sheets

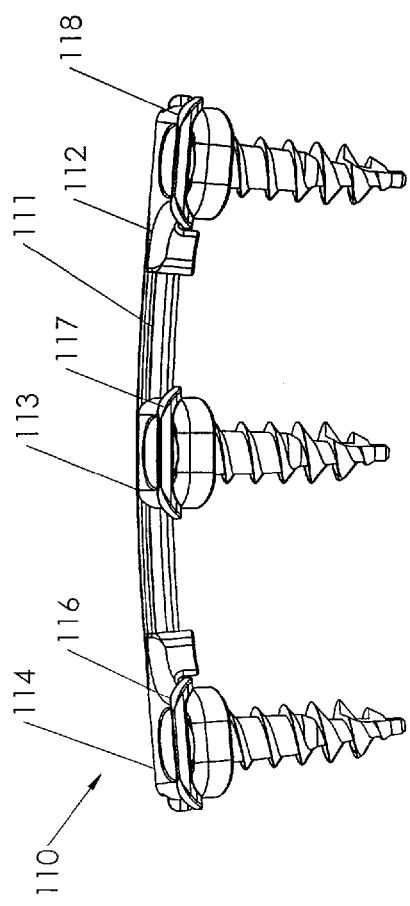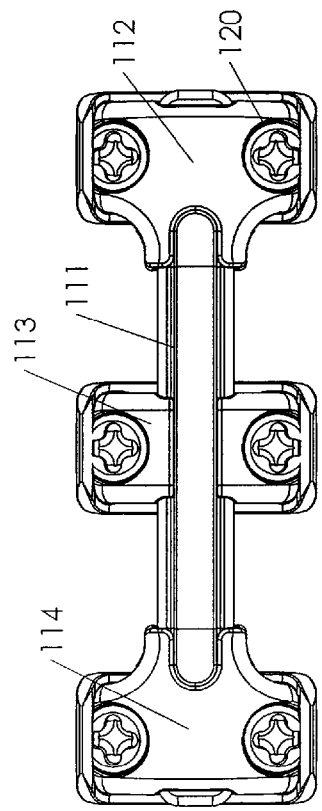
FIG. 7
FIG. 8

DYNAMIC CERVICAL PLATE WITH SPACER

CROSS-REFERENCE TO RELATED APPLICATIONS

This application claims benefit of the filing date of U.S. Provisional Patent Application No. 61/049,209 filed on Apr. 30, 2008, the contents of which are herein incorporated by reference.

BACKGROUND OF THE INVENTION

1. Field of the Invention

This invention relates to the field of orthopedic surgery and, particularly, to the area of spinal implants for stabilizing the spatial relationship of vertebrae. The device is designed for use in the cervical region of the spine though one skilled in the art may use the device in other regions of the spine and other skeletal fixations.

2. Description of the Prior Art

Spinal plates are well known in the orthopedic art for fixing bones or bone fragments in a pre-selected spatial orientation. The plates are usually attached to the bones or bone fragments by screws designed to make a secure and long lasting connection not affected by the loads caused by normal activities of the host. Gertzbein et al, U.S. Pat. No. 5,620,443, teaches an adjustable cervical connector composed of dual rods spanning the distance between adjacent vertebrae. The rods carry at least two slidable transverse connectors which are attached to the vertebrae by spikes and pedicle screws thereby fixing the relationship of the bones. The connectors are immobilized on the rods by clamps.

Richelsoph, U.S. Pat. No. 6,017,345, teaches a spinal plate spanning the distance between adjacent vertebrae. The plate has screw holes in each end. The pedicle screws are inserted through the holes and allow for some movement.

Shih et al, U.S. Pat. No. 6,136,002, teaches a similar device to that of Gertzbein with the clamps screwed onto the elongated rods.

Published Patent Application US 2003/0060828 A1 to Michelson teaches a cervical plate with at least two plate elements slidably connected together and fixed by a set screw. The contacting surfaces of the plate elements are formed with ratcheting to provide added security.

In all these prior art devices, the plate must be held in the selected position while the securing set screws or other fasteners are put in place and the final assembly is completed. Further, the prior art plates are not used in combination with spinal cages for filling the intervertebral space to compensate for removal of the spinal discs and to provide support for bone growth material and/or bone cement.

What is needed in the art is a dynamic cervical plate system that may be adjusted to length, locked in place to provide compression, and will automatically shorten its length to maintain compression. The system includes spinal cages coupled to the plate which provide intervertebral spacers for excised discs.

SUMMARY OF THE PRESENT INVENTION

Disclosed is a dynamic cervical plate system that may be adjusted to length, locked in place to provide compression, and will automatically shorten its length to maintain compression. The system includes spinal cages coupled to the plate which provide intervertebral spacers for excised discs.

Therefore, it is an objective of this invention to provide a cervical plate system with an elongated shaft adapted to span the intervertebral space and having at least two screw receivers spaced along the length of the plate. The screw receivers each have screw holes for accepting the heads of bone screws. A spinal cage is coupled to the plate and interposed between the screw receivers.

Another objective of this invention is to provide a locking mechanism that is manually operated simultaneously with the insertion of bone screws into the screw receiver to provide compression across the intervertebral space.

A further objective of this invention is to provide the locking mechanism with a retainer extending over the screw holes to prevent back out of the screws.

Yet another objective of this invention is to provide a guide rail on the plate shaft cooperating with the screw receivers and spinal cages to permit sliding connection between the screw receivers, cages and the plate shaft.

Still another objective of this invention is to provide a ratchet mechanism on the shaft and screw receivers to permit post operative one-way movement shortening the distance between the screw receivers and maintaining compression across the intervertebral space.

BRIEF DESCRIPTION OF THE DRAWINGS

FIG. 7 is a side view of a second embodiment of a cervical plate system;

FIG. 8 is a top view of the second embodiment;

DETAILED DESCRIPTION OF THE INVENTION

Figure 1:
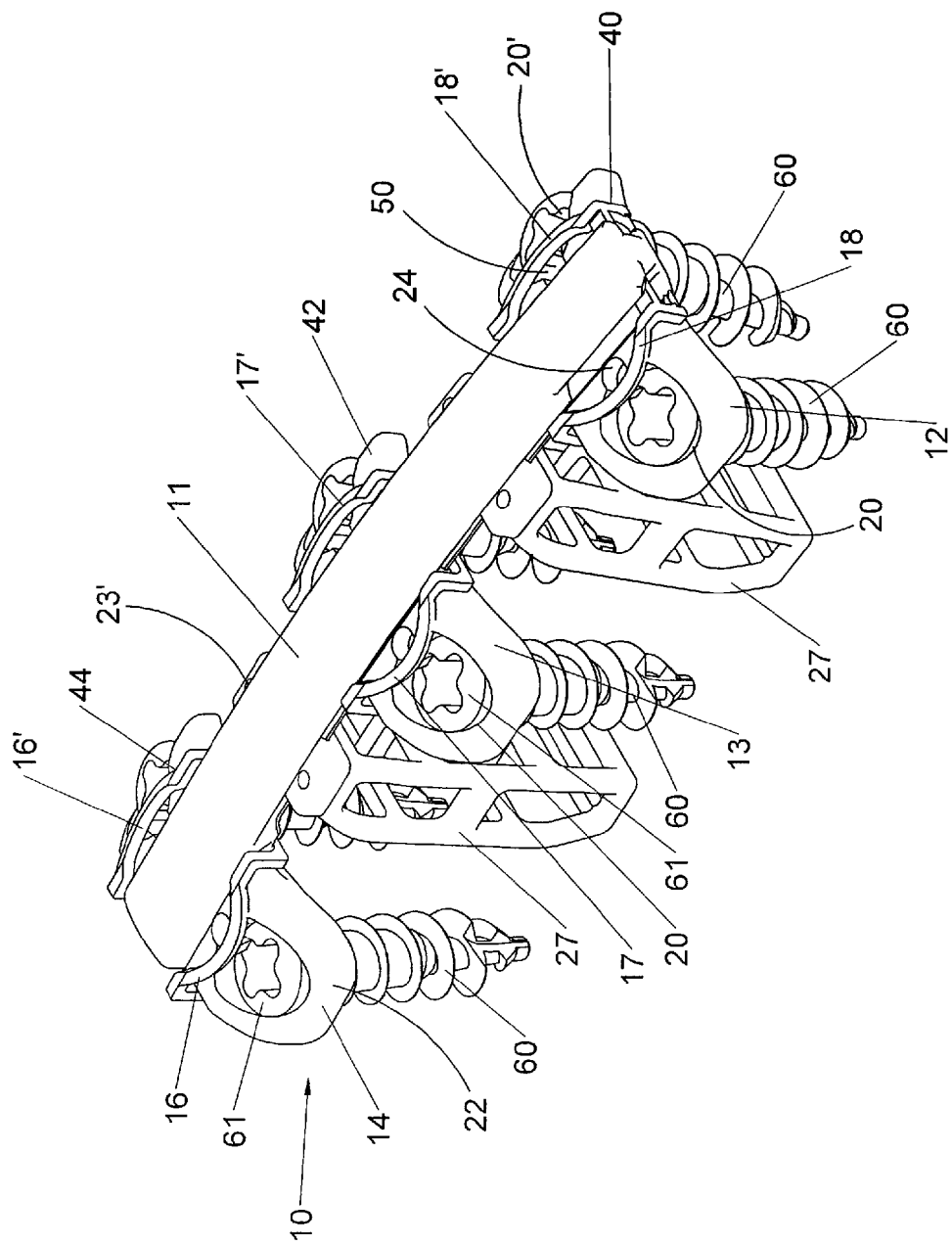
FIG. 1 is a perspective of the cervical plate system, spinal cages and screw receivers of this invention.
Figure 2:
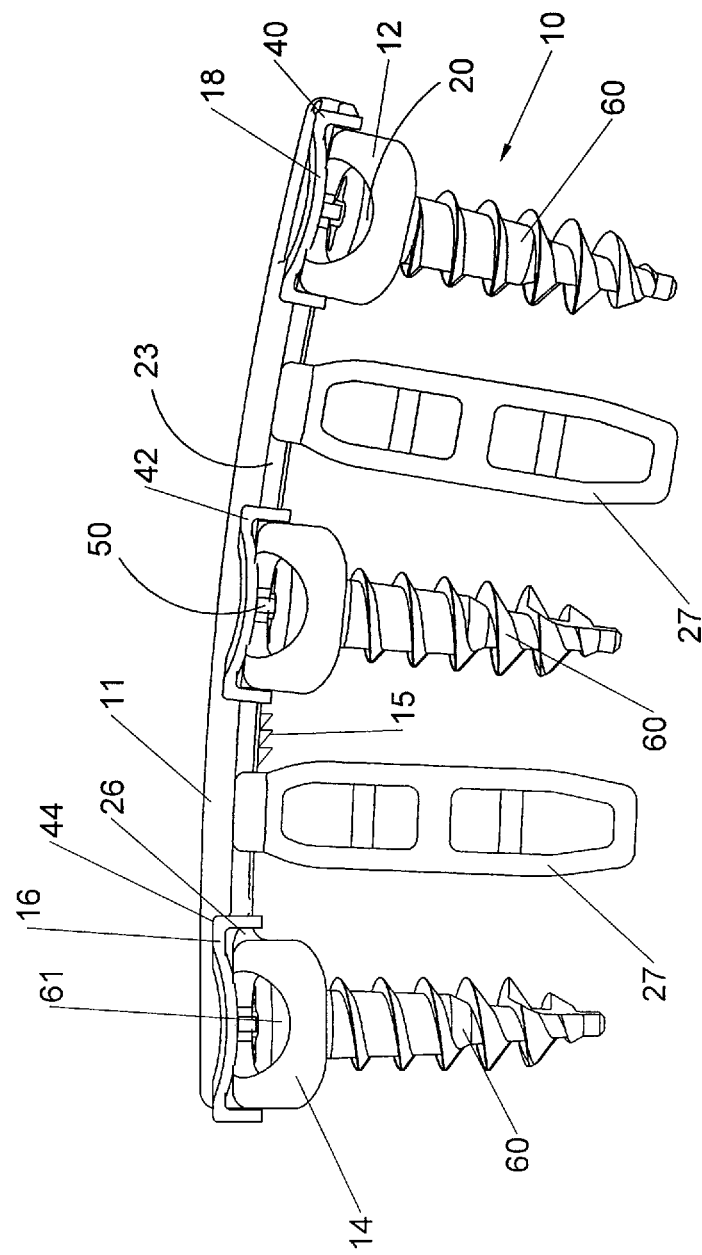
FIG. 2 is a side view of the cervical plate and screw receivers of FIG. 1.

The cervical plate 10 has an elongated flat shaft 11 that is made in different lengths but must be of a length to span, at least, the distance between two vertebrae. The plate 10 has a lateral bar 12 fixed to one end and a free end. The bar has countersunk apertures 20, 20' on each side of the elongated flat shaft for capturing the head 61 of bone screws 60. Permanently mounted to the plate is a retainer clip 40 having ears 18, 18'. The clip 40 is resilient and extends under the plate parallel but outside the periphery of the lateral bar 12 then rises vertically to the top of the flat shaft 11 and extends across the bone screw apertures 20, 20'. The portion that extends across the countersunk apertures 20, 20' are the ears 18, 18' for retaining the bone screws 60 to prevent back-out. The retainer clip 40 is resilient enough to allow flexing while the heads 61 of the bone screws 60 are seated in the aperture then is released on top of the screw heads 61. In one embodiment, the ears 18, 18' have wedges 50 which engage the edges of the screw heads 61 as the screws are tightened to further lock the screws 60 in place.

The bottom of the flat shaft 11 has a row of teeth 15 formed across the longitudinal axis of the plate 10. The teeth are angled to form a ratchet allowing one-way movement of a bar, such as 13 or 14, from the free end toward the lateral bar 12 at one end of the plate 10. In some instances, the teeth 15 may be cut normal to the shaft. Along each longitudinal side of the flat shaft are parallel grooves 23 extending from the free end toward the lateral bar.

Slidably attached to the free end of the flat shaft 11 is at least one movable bar 13 but two are preferred. The second bar 14 is of similar construction as the bar 13. Bar 13 and bar 14 have similar structure therefore; reference to elements of one bar is the same as the other.

The slidable bar 13 has a distal surface which engages the vertebrae and is convexly curved to closely fit the curvature of the vertebrae. The slidable bar 13 has apertures 20 and 20' near each end with a depression there between. The depression is approximately the same depth as the thickness of the flat shaft 11 to provide a low profile to the assembled cervical plate 10. The opposite edges of the depression have shoulders 26 that slide within the longitudinal groves 23 in the flat shaft. This provides a close association between the surface of the bar depression and the ratchet teeth 15 of the plate 10.

Attached to movable bar 13 is a retainer clip 42 having clip ears 17, 17'. The retainer clip 42 has an elongated hollow body with an oval shape. The sides of the oval follow the edges of the depression so that clip ears 17, 17' are on the proximal surface of the movable bar 13. At least one side of the clips (40, 42, 44) is welded or otherwise permanently attached to the respective side of the bars (12, 13, 14). The rounded ends of the oval of the retainer clips form the screw retainers. The pawl portions of the retainer clips extend across the flat shaft 11 engaging the teeth 15 to form the ratchet.

In the preferred embodiment, the retainer clips 42 and 44 have a flange that extends above the surfaces of the bars to provide a counter force to the bottom portion for engaging of the teeth 15 of the ratchet on the flat shaft 11. Of course, the clips may have pawls on both sides of the bar. By flexing the clip with an instrument, the flange can be disengaged from the ratchet teeth 15 for initial adjustment.

As shown in FIGS. 3 through 6 the spacers 27 have a top connector 28 having a planar base plate 29 and parallel upstanding flanges 30 which are undercut forming rails 31. An aperture 38 passes through the base plate and communicates with the hollow interior. The rails 31 slide along the groves 23 in the longitudinal edges of the flat shaft 11. The body of the spacers 27 is of open construction with a series of bars 32, 33, 34, 35 forming an open and interconnected framework about a hollow center 36. The hollow center may be filled with bone growth materials, bone particles, and/or bone cement to facilitate boney ingrowth into the intervertebral space strengthening the fusion of the several vertebrae.

Figure 3:
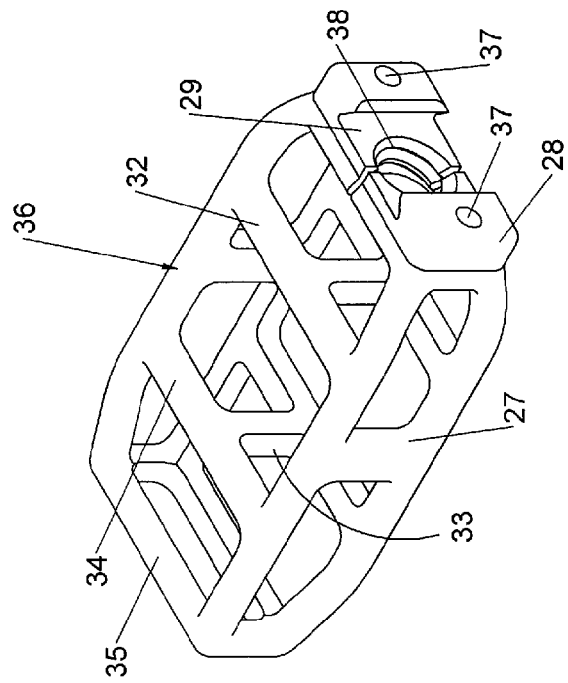
FIG. 3 is a perspective of the spinal cage of this invention.
Figure 4:
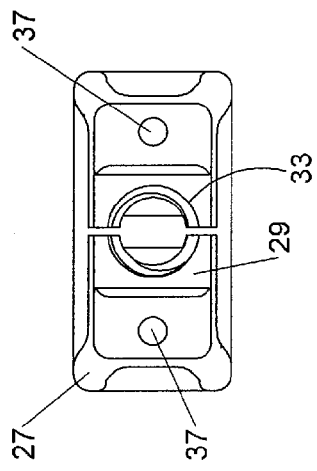
FIG. 4 is an end view of the spinal cage of FIG. 3.
Figure 5:
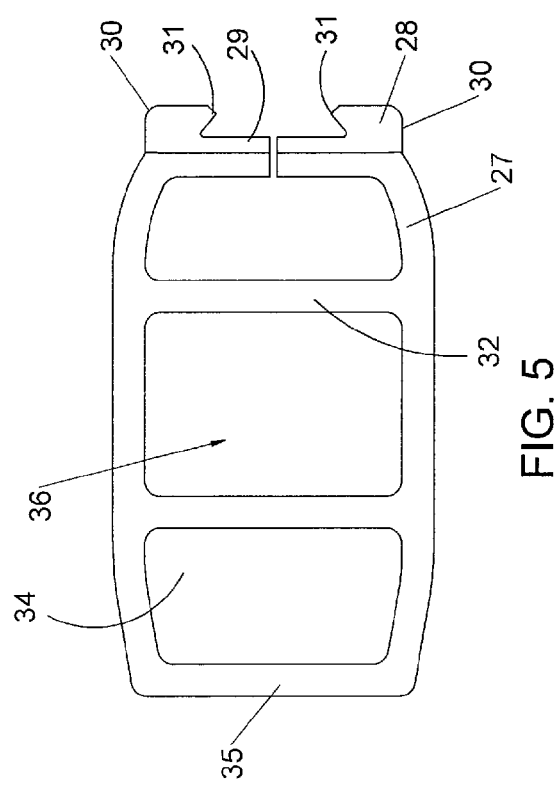
FIG. 5 is a top view of the spinal cage of FIG. 3.
Figure 6:
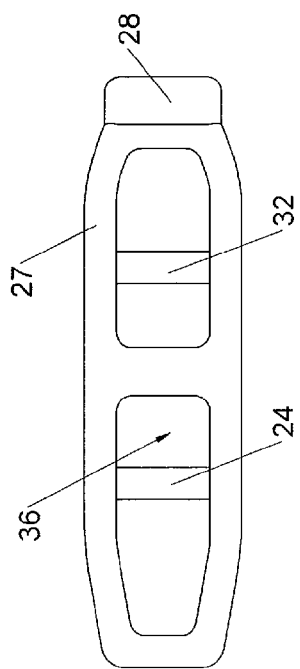
FIG. 6 is a side view of the spinal cage of FIG. 3.
Figure 9:
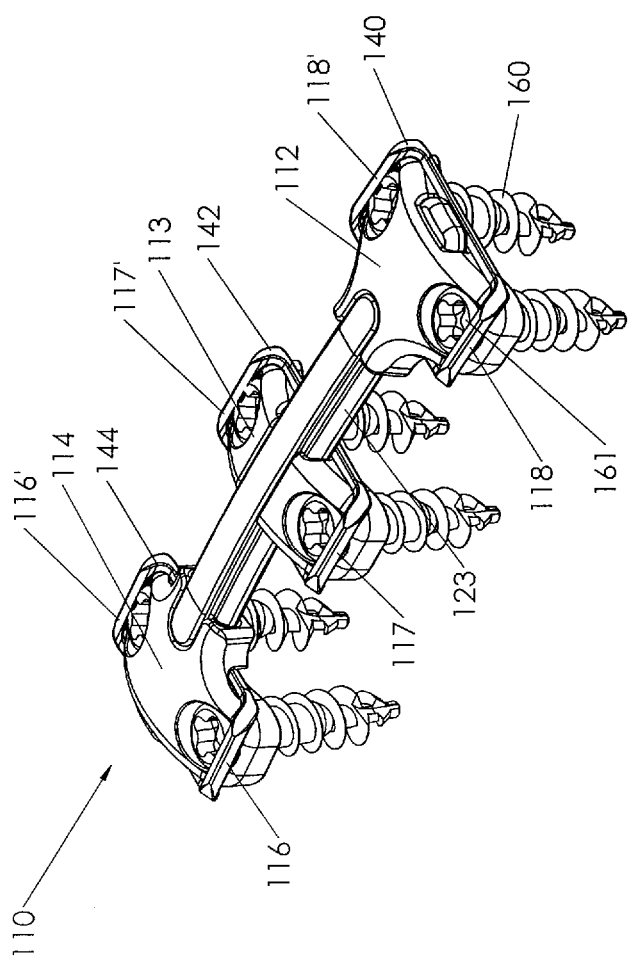
FIG. 9 is a perspective view of the second embodiment.
Figure 10:
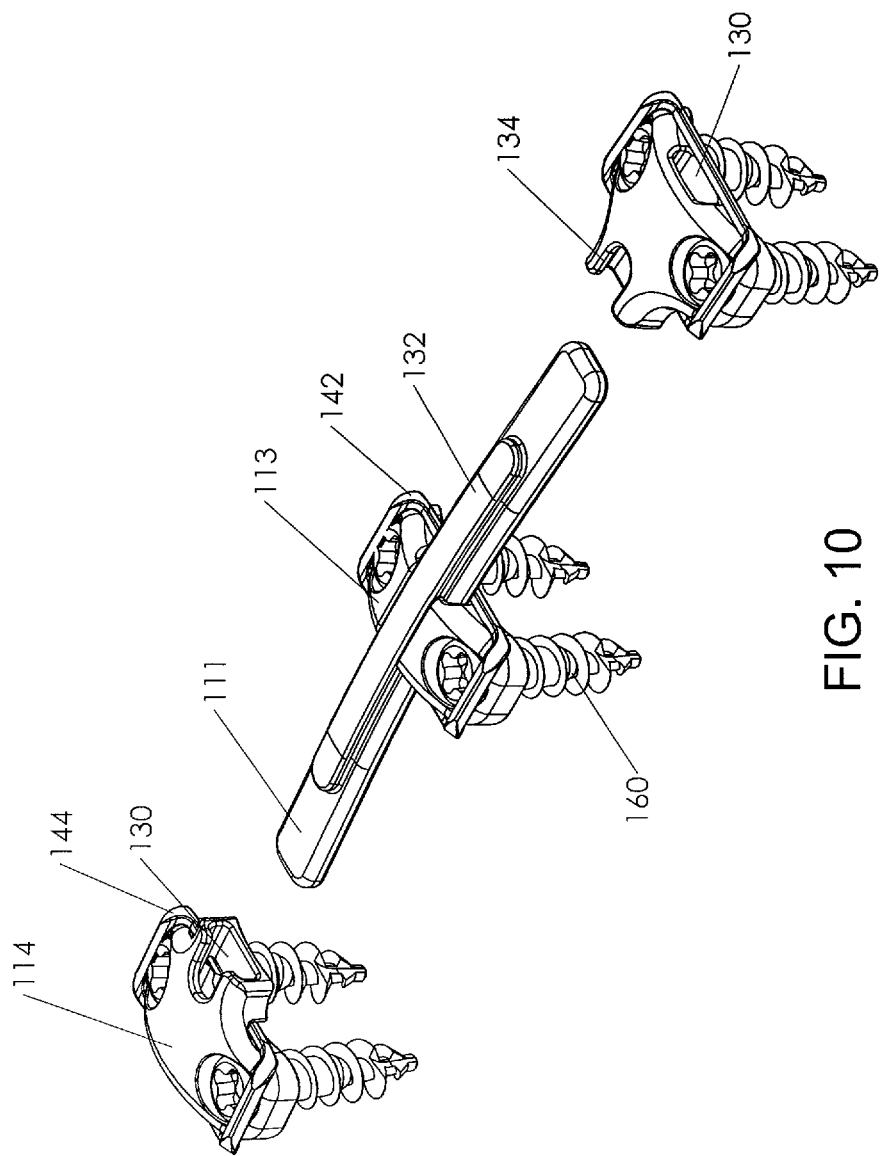
FIG. 10 is an exploded view of the second embodiment.
Figure 11:
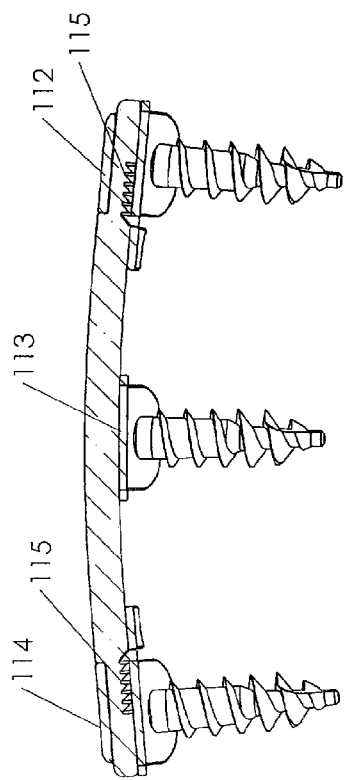
FIG. 11 is a cross sectional side view of the second embodiment.
Figure 12:
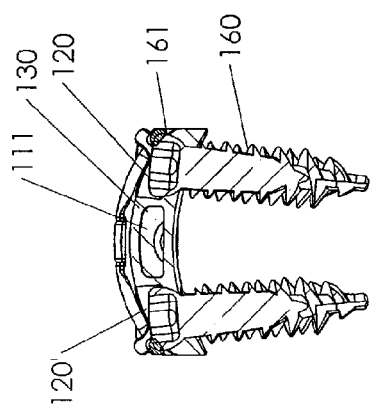
FIG. 12 is a cross sectional end view of the second embodiment.
Figure 13:
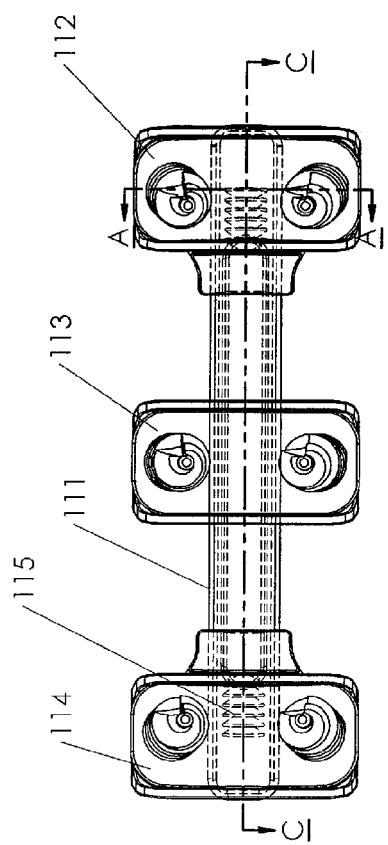
FIG. 13 is a bottom view of the second embodiment illustrating the engagement tabs.
Figure 14:
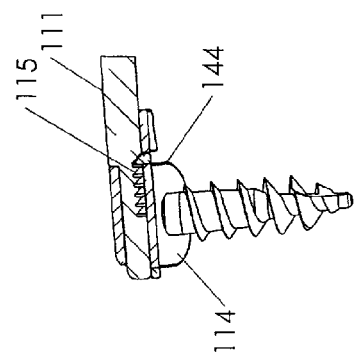
FIG. 14 is a cross sectional side view illustrating the engagement tabs.
Figure 15:
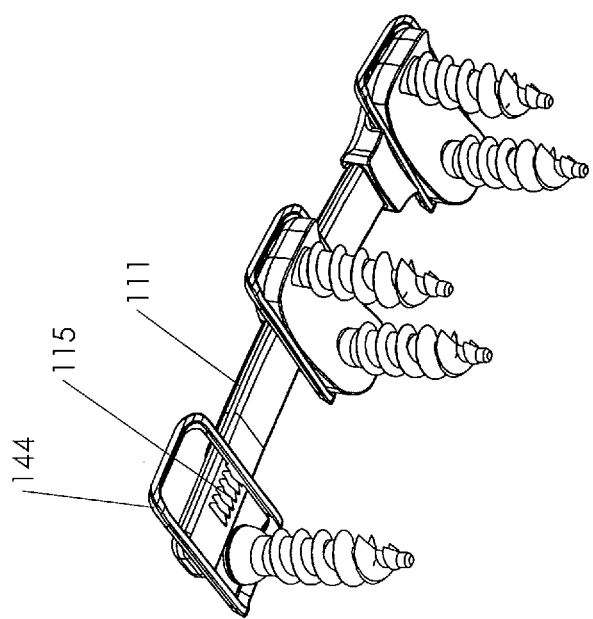
FIG. 15 is a bottom perspective view illustrating the positioning of the engagement tabs.
Figure 16:
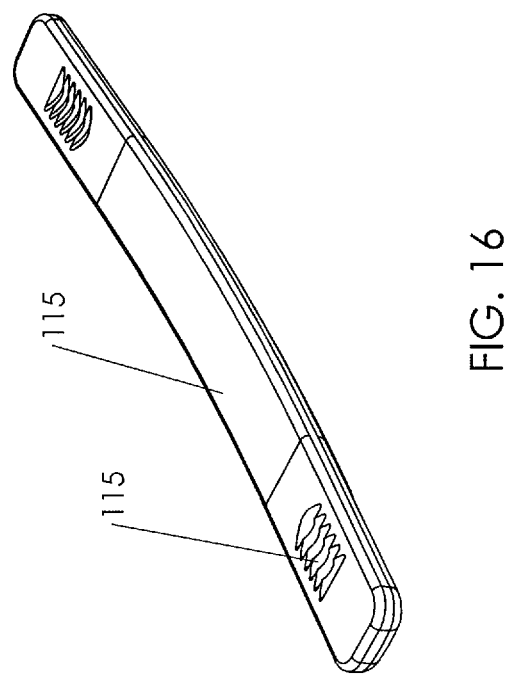
FIG. 16 is a perspective view of the connector plate.
Figure 16:
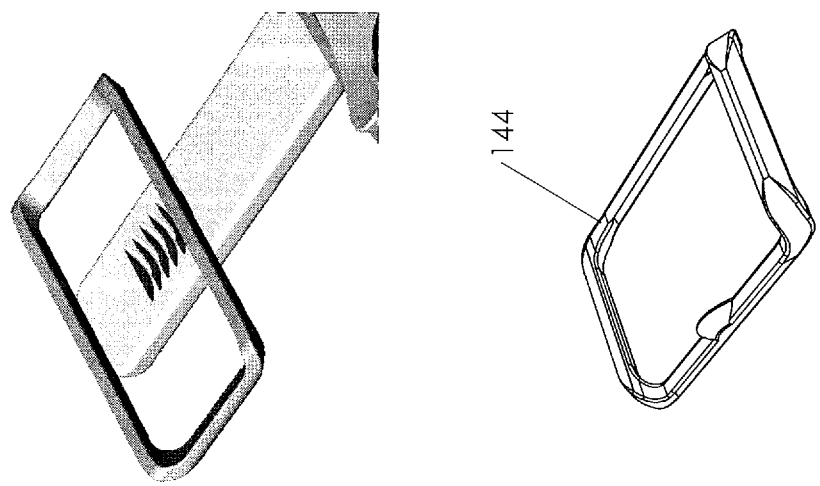

The connector 28 and the spacer 27 may be unitary or separable. As shown in FIG. 3 and FIG. 4, the connector may be permanently or separately formed and fastened to the spacer 27 by screws or brads 37. In one embodiment, the connectors, alone, could be slidably mounted on the flat shaft 11 between the bars 12, 13, or 14 as a pre-assembly. The spacers would be placed between the vertebrae, as necessary. The connectors and the spacers brought together and attached as a final assembly, in situ. Otherwise, the assembled spacers and connectors are placed between vertebrae and the plate is slidably adjusted for best placement of the bone screws in adjacent vertebrae.

In operation, the vertebrae are manipulated into the desired position and the spacers placed as required to compensate for removal of bone and/or disc material. The plate 10 is placed on the spine and the connectors 28 and the bars 13 and 14 are adjusted to provide some compression on the site to assist in the grafting of the spine. The connectors 28 are slid along the plate 10 until registered with the tops of the spacers 27. The connectors 28 can then be attached to the spacers 27. As the bars are slid along the shaft, the shoulders of the bars 13 and 14 and the grooves on the shaft maintain a close fit between the pawls and the teeth 15 on the flat shaft 11 shaft requiring the pawls to be deflected by the teeth. Once the bars are in the desired location and the flanges seated in the teeth 15, the ratchet prevents retrograde movement of the bars away from the head. The bone screws are driven into the spine. As the screw heads 61 engage the apertures the clip retainers 40, 42, and 44 are flexed to permit the screw heads 61 to seat in the apertures 20 and released to block back-out.

FIGS. 7 through 16 show a second embodiment of the invention. Bone plate 110 that includes a flat shaft 111 including three lateral bars; 112, 113, and 114 are mounted thereon. Flat shaft 111 is made in varying lengths however it has a length at least sufficient to span the distance between two adjacent vertebrae. The bone plate 110 has a fixed lateral bar 113 located between two moveable lateral bars 112 and 114. Each lateral bar has countersunk apertures 120 and 120' on each side of the flat shaft 111 for capturing the head 161 of bones screws 160. Permanently mounted to flat shaft 111 is a retainer clip 142 having retaining clip ears 117 and 117'. The retaining clip is resilient and extends under the flat shaft 111 parallel but outside the periphery of the lateral bar 113 and then rises vertically to the top of the plate and extends across the bone screw apertures 120 and 120'. Retainer clip ears 117 and 117' extend across countersunk apertures 120 and 120' for retaining the bone screws 160 and preventing them from backing out. The retainer 142 is resilient enough to allow flexing while the heads of the bone screws are being seated in the aperture and then subsequently released on to the top of the screws heads when the screws are seated within the aperture.

The bottom of the flat shaft 111 has two rows of teeth 115 formed across the longitudinal axis of the flat shaft, one at each end of the flat shaft. The teeth 115 are angled to form a ratchet allowing one-way movement of the lateral bars 112 and 114 towards the fixed lateral bar 113. Lateral bars 112 and 114 have similar structure therefore reference to elements of one bar is the same as the other. Movable lateral bars 112 and 114 have a distal surface which engages the vertebrae and are convexly curved to fit the curvature of the vertebrae. Each of lateral bars 112 and 114 has an internal passageway 130 located between its distal and proximal surfaces. Internal passageway 130 is sized to closely conform to the external dimensions of the flat shaft 111 at each end. The ends of flat shaft 111 are somewhat reduced in size from the remainder of the flat shaft 111. The proximal surface of flat shaft 111 also includes a longitudinally extending projection 132; the ends which conform in size to a complimentary recess 134 formed in each of the proximal surface of the lateral bars 112 and 114. Attached to movable bar 112 is a retainer clip 140 having retainer clip ears 118 and 118'. Attached to movable bar 114 is a retainer clip 144 having retainer clip ears 116 and 116'. The retainer clips 140 and 144 each have an elongated hollow body with an oval shape. The sides of the oval follow the edges of bar so that the retainer clip ears 118 and 118' are on the proximal surface of the moveable bar 112 and retainers clip ears 116 and 116' are on the proximal surface of movable bar 114. Each of the retaining clip ears prevent the screws from backing out. The pawl portion of the retaining clips 140 and 144 extend across the flat shaft 111 engaging the teeth 115 formed at each end thereof to from the ratchet. The retaining clips 140 and 144 each have a flange that extends above the surface of the associated movable bars to provide a force for engaging the teeth 115 formed on the bottom surface on each end of the flat shaft 111. By flexing the retainer clip with an instrument, the flange can be disengaged from the teeth 115 for initial adjustment.

While not illustrated, the spacers 27 disclosed above and shown in FIGS. 3 through 6 can be used in the bone plate arrangement 110 disclosed in FIGS. 7 through 16. In this arrangement the upstanding flanges and rails on the top connectors are configured to be operatively connected to rail 111.

It is well known that as the site heals and the adjacent vertebrae begin to graft together and as a result of the forces of gravity, there is some reduction in the span between the vertebrae. As this occurs, the dynamic cervical plate can accommodate the reduction and maintain some compression because the shaft will move in the bars resulting in the clips moving from one ratchet tooth to the next automatically shortening the intervertebral distance.

A number of embodiments of the present invention have been described. Nevertheless, it will be understood that various modifications may be made without departing from the spirit and scope of the invention.

What is claimed is:

1. A dynamic cervical plate comprising:
   a flat elongated shaft having grooved opposite side edges along a longitudinal length sufficient to span an intervertebral space between a first end and a second end, said shaft further defined by a proximal and a distal surface, said distal surface including a row of teeth formed across the longitudinal axis;
   a lateral bar fixed to said flat elongated shaft, said fixed lateral bar having a pair of apertures positioned adjacent to said opposite side edges of said flat elongated shaft adapted to receive bone screws, said fixed lateral bar including a first retainer clip having flexible clip ears that overlie an outer portion of each aperture for maintaining an inserted bone screw by flexing of said first retainer clip ears upon insertion of the bone screw;
   at least one movable lateral bar slidably attached to said flat elongated shaft, said movable lateral bar having a pair of apertures positioned adjacent to said opposite side edges of said flat elongated shaft adapted to receive bone screws, each said movable lateral bar including a second retainer clip having flexible clip ears that overlie a outer portion of each aperture for maintaining an inserted bone screw by flexing said clip ears upon insertion of the bone screw, said clip ears overlying the head of the bone screws to prevent back-out, and a flange formed in said second retainer clip for engaging said shaft teeth, said flange constructed and arranged to permit unidirectional movement of said movable lateral bar towards said fixed lateral bar;
   a spacer member removably fastened to a connector member, said connector member operatively connecting said spacer member to said flat elongated shaft, said connector member including a pair of upstanding flanges, said upstanding flanges operatively engage said grooves on said flat elongated shaft, said spacer member configured to be inserted into an intervertebral space located along said flat elongated shaft between said fixed lateral bar and said movable lateral bar.

2. The dynamic cervical plate of claim 1 wherein said fixed lateral bar and said movable lateral bar each have a depression formed between said apertures, said depression having a depth equal to a thickness of said flat shaft, said depression having opposite edges forming a pair of shoulders, each shoulder operatively engaging one of said grooves.

3. The dynamic cervical plate of claim 1 wherein said spacer member and connector member are formed as a unitary member.

4. The dynamic cervical plate of claim 1 wherein said spacer member is of open construction with a series of bars forming an open and interconnected framework about a hollow center, wherein said hollow center may be filled with bone growth materials, bone particles and or bone cement to facilitate boney ingrowth into the intervertebral space strengthening the fusion of several vertebrae.

5. The dynamic cervical plate of claim 1 further including a first said spacer member located between said fixed lateral bar and said first movable lateral bar and a second said spacer member located between said first movable lateral bar and said second movable lateral bar.

6. The dynamic cervical plate of claim 1, wherein said fixed lateral bar is positioned on said flat elongated shaft between said first movable lateral bar and said second movable lateral bar.

7. The dynamic cervical plate of claim 6, further including a first said spacer member located between said fixed lateral bar and said first movable lateral bar and a second said spacer member located between said fixed lateral bar and said second movable lateral bar.

8. The dynamic cervical plate of claim 6 wherein each of said movable lateral bars has an internal passageway located between its distal and proximal surfaces, said internal passageway being sized to closely conform to the external dimensions of said flat elongated shaft at each end thereof.

9. The dynamic cervical plate of claim 6 wherein said flat elongated shaft further includes a second row of teeth formed across the longitudinal axis of said flat elongated shaft; a third retainer clip mounted on said second movable lateral bar including a flange engaging said second row of teeth to allow one way movement of said second movable lateral bar towards said fixed lateral bar.

10. The dynamic cervical plate of claim 1 wherein said flat elongated shaft further includes a second row of teeth formed across the longitudinal axis of said flat elongated shaft; a third retainer clip mounted on said second movable lateral bar including a flange engaging said second row of teeth to allow one way movement of said second movable lateral bar towards said fixed lateral bar.

\* \* \* \* \*